United States Patent [19]

Tamura et al.

[11] Patent Number: 5,082,467
[45] Date of Patent: Jan. 21, 1992

[54] DYE COMPOSITION FOR KERATINOUS FIBERS

[75] Inventors: Tadashi Tamura; Akira Kiyomine; Michio Tanaka; Yoshinori Nishizawa, all of Ichikai; Hidetoshi Tagami, Tokyo; Masahiko Ogawa, Tokyo; Toru Yoshihara, Tokyo; Tsutomu Muraoka, Tokyo; Jiro Kawase, Tokyo, all of Japan

[73] Assignee: Kao Corporation, Tokyo, Japan

[21] Appl. No.: 645,821

[22] Filed: Jan. 25, 1991

[30] Foreign Application Priority Data

Feb. 8, 1990 [JP] Japan .................................. 2-28829
Dec. 21, 1990 [JP] Japan ................................ 2-412660
Dec. 21, 1990 [JP] Japan ................................ 2-412661

[51] Int. Cl.$^5$ .................... A61K 7/13; C07D 213/04; C07D 213/22; C07C 321/00
[52] U.S. Cl. ........................................ 8/409; 8/405; 8/406; 8/412; 8/414; 8/415; 8/416; 546/255; 546/258; 564/441
[58] Field of Search ................... 8/405, 406, 409, 410, 8/412, 413, 414, 415, 416; 564/441; 546/255, 258

[56] References Cited

U.S. PATENT DOCUMENTS 4,473,375 9/1984 Clausen .................................. 8/409
4,661,115 4/1987 Orth et al. ............................. 8/409
4,754,069 6/1988 Braun et al. ........................... 8/410

FOREIGN PATENT DOCUMENTS 1492158 1/1970 Fed. Rep. of Germany.
1617835 4/1972 Fed. Rep. of Germany.
2445002 4/1975 Fed. Rep. of Germany.
2714831 10/1978 Fed. Rep. of Germany.

OTHER PUBLICATIONS

Chemical Abstracts, vol. 60, No. 7, Mar. 30, 1964, Columbus, Ohio, U.S.A. J. Barycky et al., "Preparation of 2-Alkoxy-3,5,-Diamino-Pyridines", col. 7987, Abstract-No. 7 987e & Roczniki Chem. 1963, 37 (11) 1 443-6.
Chemical Abstracts, vol. 91, No. 16, Oct., U.S.A. T. Ebara et al., "Dyes Containing Diamino-4-Ethyl-Pyridines", p. 348, col. 1,2, Abstract-No. 128 898v & Japan Kokai Tokkyo Koho 79 32, 535.
Chemical Abstracts, vol. 81, No. 20, Nov. 18, 1974, Columbus, Ohio, U.S.A. T. Ebara et al., "Hair Dyes Containing 3,5-Diamino-Pyridine", p. 416, col. 2, Abstract-No. 126 686u & Japan Kokai 74 50, 144.
Chemical Abstracts, vol. 74, No. 11, Mar. 15, 1971, Columbus, Ohio, U.S.A. D. J. Brown et al., "Aza Analogs of Pteridine", p. 362, col. 1, Abstract-No. 53 735b & J. Chem. Soc., C 1970 (19) 2 661-6.
Chemical Abstracts, vol. 98, No. 8, Feb. 21, 1983, Columbus, Ohio, U.S.A. R. Twieg et al., "Organic Materials for Nonlinear Optics, Nitropyridine Derivatives", p. 542, col. 2, Abstract-No. 62 879a & Chem. Phys. Lett. 1982, 92(2), 208-11.
Chemical Abstracts, vol. 93, No. 3, Jul. 21, 1980, Columbus, Ohio, U.S.A. J. Kozil et al., "Chargetransfer Complexes with Pyridine Analogs of Picric Acid Sym--Trinitrobenzene and Trinitroanisole", p. 616, col. 1, Abstract-No. 25 412u & Bull. Acad. Pol. Sci., Ser. Chim. 1979, 27(5), 335-4.

Primary Examiner—Paul Lieberman
Assistant Examiner—William S. Parks
Attorney, Agent, or Firm—Oblon, Spivak, McClelland, Maier & Neustadt

[57] ABSTRACT

A dye composition for keratinous fibers is disclosed. The composition comprises a developing substance and, as a coupling substance, a 3,5-diaminopyridine derivative of the following formula (I),

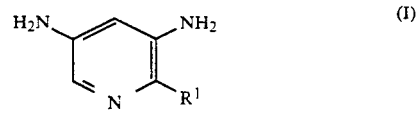
(I)

wherein $R^1$ is an alkoxy group or a group

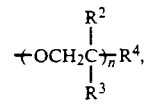

wherein $R^2$ and $R^3$ may be the same or different and individually represents a hydrogen atom or a hydroxyalkyl group, $R^4$ a hydroxy, alkoxy, or hydroxyalkyl group, and n is a number of 1–4; or a salt thereof. The composition is capable of dyeing keratinous fibers such as hairs in blue color with a high vividness and with resistances to the light, color change, and discoloration due to shampooing.

3 Claims, No Drawings

DYE COMPOSITION FOR KERATINOUS FIBERS

BACKGROUND OF THE INVENTION

1. Field of the Invention

This invention relates to a dye composition for keratinous fibers, and, more particularly, to a dye composition for keratinous fibers which is capable of dyeing keratinous fibers to a strong tone. The present invention also relates to a novel 3,5-diaminopyridine derivative which is useful as a developing substance for said dye composition and to an intermediate for producing the 3,5-diaminopyridine derivative.

2. Description of the Background Art

Oxidizing dyes, in which a developing substance and a coupling substance are employed in combination, have been widely used for dyeing keratinous fibers such as hair or the like. These oxidizing dyes make use of oxidizing coloring substances produced by the oxidizing-coupling reaction of a developing substance and a coupling substance for strongly dyeing keratinous fibers such as hair or the like. Paraphenylenediamine derivatives, p-aminophenol derivatives, diaminopyridine derivatives, 4-aminopyrazolone derivatives, hetero-cyclic hydrazone, and the like are used as the developing substance. Given as the coupling substances which are used are o-naphthol, o-cresol, m-cresol, 2,6-dimethylphenol, 2,5-dimethylphenol, 3,4-dimethylphenol, 3,5-dimethylphenol, benzcatechin, pyrogallol, 1,5-dihydroxynaphthalene, 1,7-dihydroxy-naphthalene, 5-amino-2-methylphenol, hydroquinone, 2,4-diaminoanisole, m-toluylenediamine, o-aminophenol, resorcin, resorcin-monomethylether, m-phenylenediamine, 1-phenyl-3-methyl-5-pyrazolone, 1-phenyl-3-amino-5-pyrazolone, 1-phenyl-3,5-diketopyrazolidine, 1-methyl-7-dimethylamino-4-hydroxyquinolone-2, 1-amino-3-cyanacetylamino-4-nitrobenzole, m-aminophenol, 4-chlororesorcin, 2-methylresorcin, 2,4-diaminophenoxyethanol, 2,6-diaminopyridine, 3,5-diaminotrifluoromethylbenzene, 2,4-diamino-6-hydroxypyrimidine, 2,4,6-triaminopyrimidine, 2-amino-4,6-diamino-2-hydroxypyrimidine, p-nitro-o-phenylenediamine, 2-amino-5-nitrophenol, p-nitro-m-phenylenediamine, o-nitro-p-phenylenediamine, 2-amino-4-nitrophenol, and the like.

These conventional oxidizing dyes have defects in their performance which are yet to be satisfied in terms of saturation or vividness of colors, dyeing capability, and fastness. Since these characteristics of oxidizing dyes are greatly affected by the coupling substances, it is extremely important to develop a coupling substance having superior characteristics to obtain a good oxidizing dye.

Among conventional blue color oxidizing dyes those in which m-phenylenediamine or 2,6-diaminopyridine is used as a coupling subsantce are known to give a blue color with high vividness. These dyes, however, involve remarkable color changes after the dyeing and discoloration due to shampooing. There has been a strong desire for the development of a dye composition for keratinous fibers giving an excellent vivid blue color and superior fastness.

In view of this situation, the present inventors have synthesized a variety of compounds and investigated their performance as a coupling substance. As a result, the inventors found that a specific type of 3,5-diaminopyridine derivatives or their salts satisfied the above requirement in a coupling substance. This finding has led to the completion of this invention.

SUMMARY OF THE INVENTION

Accordingly, an object of this invention is to provide a dye composition for keratinous fibers comprising a developing substance and, as a coupling substance, a 3,5-diaminopyridine derivative of the following formula (I),

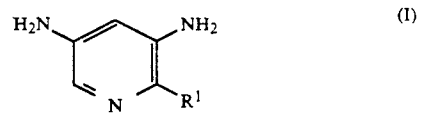

wherein $R^1$ is an alkoxy group or a group

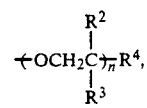

wherein $R^2$ and $R^3$ may be the same or different and individually represents a hydrogen atom or a hydroxyalkyl group, $R^4$ represents a hydroxy, alkoxy, or hydroxyalkyl group, and n is a number of 1-4; or a salt thereof.

Among the 3,5-diaminopyridine derivatives of formula (I), those having a specific substituent $R^1$ are novel compounds.

Accordingly, another object of the present invention is to provide a 3,5-diaminopyridine derivative of the following formula (II),

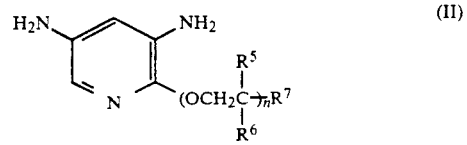

wherein $R^5$ and $R^6$ may be the same or different and individually represents a hydrogen atom or a hydroxyalkyl group, $R^7$ is a hydroxy, alkoxy, or hydroxyalkyl group, and n is a number of 1-4; or a salt thereof.

Certain 3,5-dinitropyridine derivatives for producing the 3,5-diaminopyridine derivatives of formula (II) are novel compounds.

Accordingly, a still another object of the present invention is to provide a 3,5-dinitropyridine derivative of the following formula (III),

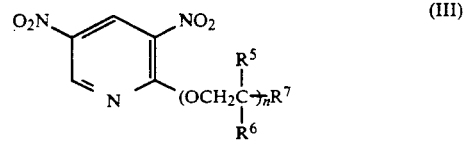

wherein $R^5$, $R^6$, $R^7$, and n have the same meanings as defined in formula (II); or a salt thereof.

DETAILED DESCRIPTION OF THE INVENTION AND PREFERRED EMBODIMENTS

Given as preferable examples of alkoxy groups represented by $R^1$ and $R^4$ in formula (I) of a 3,5-diamino-pyridine derivative, which is a coupling substance of the present invention, are alkoxy groups having 1-15 carbon atom, e.g. methoxy, ethoxy, n-propyloxy, isopropyloxy, n-butyloxy, t-butyloxy, pentyloxy, octyloxy, and dodecyloxy groups. Examples of hydroxyalkyl groups which are represented by $R^2$, $R^3$ and $R^4$ in formula (I) include hydroxyalkyl groups having 1-15 carbon atom, e.g. hydroxymethyl, $\beta$-hydroxyethyl, $\gamma$-hydroxypropyl, and 2,3-dihydroxypropyl groups. These examples of $R^1$-$R^4$ in formula (I) applies in the same way to $R^5$-$R^7$ in formulas (II) and (III).

The 3,5-diaminopyridine derivative of formula (I) can be prepared, for example, according to the following reaction scheme.

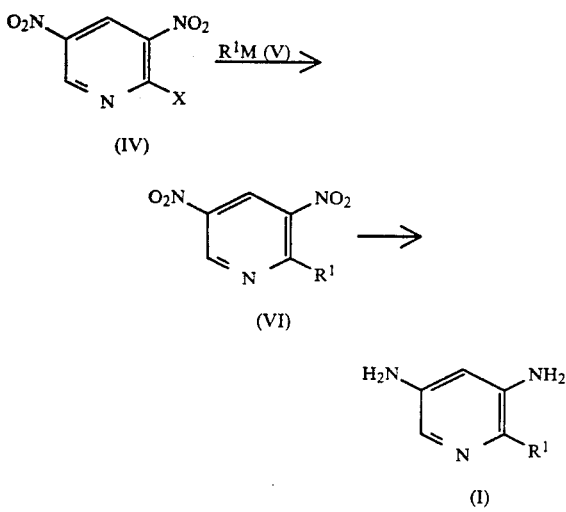

wherein X is a halogen atom, M is an alkali metal, and $R^1$ has the same meaning as previously defined.

According to the above reaction scheme, 2-halogeno-3,5-dinitropyridine (IV) and a metal alkoxide (V) are reacted to produce compound (VI). Compound (VI) is then hydrogenated to give 3,5-diaminopyridine derivative of formula (I).

2-Chloro-3,5-dinitropyridine is given as an example of 2-halogeno-3,5-dinitropyridine (IV) which is the raw material of the above reaction. As examples of metal alkoxide (V), sodium alkoxides which are produced by the reaction of sodium hydride or a metallic sodium and an alcohol are given.

The reaction of compound (IV) and compound (V) is carried out, for example, in the presence of a solvent such as an alcohol by stirring the mixture at $-5°$ C. to room temperature for about 5 minutes to 5 hours. The hydrogenation of compound (VI) to produce the target 3,5-diaminopyridine derivative is carried out according to a conventional hydrogenation process of nitro group, e.g. catalytic hydrogenation using palladium carbon.

The 3,5-diaminopyridine derivative (I) thus prepared can be used in the form of a salt for easiness in incorporation into a final product. Preferable salts are the salts of inorganic or organic acid such as hydrochloric acid, sulfuric acid, phosphoric acid, acetic acid, propionic acid, lactic acid, citric acid, and the like.

Any developing substances which are used in a conventional oxidizing dye can be used in the dye composition of the present invention. Examples of such developing substances are p-phenylenediamine, toluene-2,5-diamine, N-phenyl-p-phenylenediamine, p-aminophenol, methoxy-p-phenylenediamine, 2,5-diaminopyridine, p-methylaminophenol, tetraaminopyrimidine, 2,4-diaminophenol, o-aminophenol, o-chloro-p-phenylene-diamine, 4,4'-diaminodiphenylamine, and the like. Of these, p-phenylenediamine, toluene-2,5-diamine, N-phenyl-p-phenylenediamine, methoxy-p-phenylenediamine, and o-chloro-p-phenylenediamine are especially preferable.

A desirable proportion of the 3,5-diaminopyridine derivative (I) or its salt and a developing substance in the dye composition of the present invention is in the range of about 1:0.5 to 1:2 in molar ratio. Excessive use of one component to the other is allowable in this range. One type of developing substance and coupling substance can be employed either independently or in combination with one or more other types of developing substances or coupling substances.

In addition to the above-mentioned developing substances or coupling substances, any known developing substances, conventional direct dyes, or the like can be formulated to the composition of this invention, if necessary for producing a desired color tone.

Hair or other materials are colored by the dye composition of this invention through an oxidizing coupling reaction of the components with the aid of oxygen in the air. Effecting the oxidizing coupling reaction with the aid of a chemical oxidizing agent, however, is more desirable. Especially preferably oxidizing agents are hydrogen peroxide, hydrogen peroxide-adduct of urea, melamine, or sodium borate, or a mixture of one of these hydrogen peroxide-adducts and potassium peroxidedisulfate, and the like.

It is usually desirable to provide the dye composition of this invention in the form of a cream, emulsion, gel, solution, or the like. Preparing the composition in such forms can be accomplished according to the conventional methods. In this instance, in addition to the developing substances and coupling substances, various ingredients which are commonly used in cosmetics are formulated into the composition. Such ingredients include wetting agents (emulsifiers), solubilizing agents, viscosity increasing agents, stabilizers, tactile sense improvers, hair conditionig base components, perfumes, and the like. Wetting agents (emulsifiers) used in the composition include, for example, alkylbenzenesulfonates, fatty alcohol sulfates, alkylsufonates, fatty acid alkanolamides, ehtylene oxide adducts of fatty alcohol, and the like. Given as examples of viscosity increasing agents are methyl cellulose, starch, higher fatty alcohols, paraffin oils, fatty acids, and the like. Examples of stabilizers include reducing agents (e.g., sulfites), hydroquinone derivatives, chelating agents, and the like. Tactile sense improvers and hair conditioning base components are typified by silicones, higher alcohols, various kinds of nonionic surface active agents and cationic polymers, and the like.

The amounts of the developing substances and coupling substances to be formulated into the above-mentioned form of the invented composition are 0.001 to 10% by weight, and preferably 0.01 to 5% by weight. The desirable amount of wetting agents (emulsifiers) and viscosity increasing agents in the composition is usually 0.5 to 30% by weight and 0.1 to 25% by weight, respectively.

A typical procedure for dyeing keratinous fibers using the dye composition of this invention is now illustrated. A dye fluid is first prepared by adding an oxidizing agent to the dye composition to effect oxidizing coupling of the mixture. This dye fluid is applied to the subject keratinous fibers, which are then allowed to stand for about 5 to 50 minutes, preferably 25 to 35 minutes, to effect the action of the dye onto the fibers. The keratinous fibers thus sufficiently dyed ar finally washed and dried. It is desirable that the temperature of the dye fluid be maintained between 15 to 40° C.

It is possible to obtain a blue color with a high degree of vividness by dyeing keratinous fibers by the use of the dye composition in which a 3,5-diaminopyridine derivative (I) or its salt is used as a coupling substance. In addition, the color produced possesses excellent light resistance, washing resistance, and wear resistance.

Other features of the invention will become apparent in the course of the following description of the exemplary embodiments which are given for illustration of the invention and which are not intended to be limiting thereof.

EXAMPLES

Synthetic Example 1

(1) Preparation of 2-hydroxy-3-(3,5-dinitro-2-pyridyloxy)-propanol 3.3 g of sodium hydride (60% in oil, 82.5 mmol) which had been washed with hexane was dispersed in 150 ml of toluene under a nitrogen atmosphere, and to this suspension was dropwise added 7.5 g of glycerol while stirring with a mechanical stirrer to precipitate sodium alcholate. After completion of the addition, the stirring was continued for 30 minutes, followed by decantation to remove toluene and an addition of 150 ml of glycerol to the residue. After stirring for 15 minutes, 15 g of 2-chloro-3,5-dinitropyridine (73.7 mmol) was added by portions under ice-cooling. The mixture was stirred for 1 hour under ice-cooling and for a further 1 hour at room temperature, followed by an addition of 35 ml of saturated aqueous solution of ammonium chloride and extraction with ethyl acetate. The extract was washed with saturated brine and dried over anhydrous sodium sulfate. The solvent was removed by evaporation and the residue was purified over silica gel column chromatography (Silica gel 60 manufactured by Merk Co.; eluent: ethyl acetate:hexane = 1:1–2:1) to obtain 19 g (73.2 mmol) of the title compound in the form of a yellow solid (yield: 99%). The compound can be further purified by a mixed solvent of ethanol-ether-hexane.

m.p. 65–67° C.

$^1$H-NMR (200 MHz, DMSO-d$_6$) δppm; 3.47(2H, t, J=5.6Hz), 3.8–3.9(1H, m), 4.51(1H, dd, J=10.9Hz, 5.8Hz), 4.63(1H, dd, J=10.9Hz, 4.1Hz), 4.74(1H, t, J=5.6Hz), 5.07(1H, d, J=5.1Hz), 9.13(1H, d, J=2.0Hz), 9.35(1H, d, J=2.0Hz).

IR (KBr)νcm$^{-1}$: 3400, 3088, 2938, 1617, 1518, 1341.

Elemental Analysis (for C$_8$H$_9$N$_3$O$_7$):
Calculated: C: 37.07%, H: 3.50%, N: 16.21%
Found: C: 37.03%, H: 3.42%, N: 16.26%

(2) Preparation of 3-(3,5-diamino-2-pyridyloxy)-2-hydroxy-propanol dihydrochloride 4.6 g (17.7 mol) of 2-hydroxy-3-(3,5-dinitro-2-pyridyloxy)-propanol, 300 ml of ethanol which had been deaerated with nitrogen gas, and 250 mg of 5% palladium carbon were placed in an autoclave. The mixture was stirred for 2 days at a hydrogen pressure of 20 atm, passed through celite to remove the catalyst, and distilled under reduced pressure to remove the solvent. The residue was purified over silica gel column chromatography (Silica gel 60 manufactured by Merk Co. eluent: ethyl acetate:methanol =5:1) and treated with activated carbon. Hydrogen chloride gas was bubbled into the solution to precipitate the salt The precipitate was washed with ether, dissolved into methanol at room temperature, and filtered. Tetrahydrofuran was added to the filtrate for the recrystallization. The crystals were dried to obtain 2.0 g (7.4 mmol) a light green solid of the title compound (yield: 42%).

m.p. 168.6–168.9° C. (decomposed)

$^1$H-NMR (200 MHz, DMSO-d$_6$)δppm; 3.46(2H, d, J=5.8Hz), 3.72–3.88(1H, m), 4.08(1H, dd, J=10.8Hz, 6.4Hz), 4.27(1H, dd, J=10.8Hz, 4.0Hz), 5.2–7.5(6H, s(br)), 6.90(1H, s), 7.36(1H, s).

IR (KBr)νcm$^{-1}$: 3460, 3274, 2920, 1572, 1290.

Elemental Analysis (for C$_8$H$_{15}$N$_3$O$_3$Cl$_2$):
Calculated: C: 35.31%, H: 5.56%, N: 15.44%, Cl: 26.06%
Found: C: 35.13%, H: 5.54%, N: 15.21%, Cl: 25.62%

Synthetic Example 2

(1) Preparation of 2-(2-methoxyethoxy)-3,5-dinitropyridine 3.22 g (140 mmol) of metallic sodium was added to 70 ml of ethylene glycol monomethyl ether under ice-cooling and the mixture was stirred until no more hydrogen gas was produced. To the solution was dropwise added 25.0 g (123 mmol) of 2-chloro-3,5-dinitropyridine in 30 ml of ethylene glycol under ice-cooling over 5 minutes. After stirring for 30 minutes, the mixture was charged into 500 ml of saturated aqueous solution of ammonium chloride, followed by extraction with 400 ml of chloroform. The organic layer was washed with saturated brine and dried over anhydrous sodium sulfate. Solvent was evaporated under reduced pressure to obtain yellow crystals. 24.5 g (101 mmol) of light yellow prismal crystals of the title compound was obtained by recrystallization from ethanol (yield: 82%).

m.p. 45.5–46.5° C.

$^1$H-NMR (200 MHz, DMSO-d$_6$)δppm; 3.34(3H, s), 3.73(2H, t, J=4.5Hz), 4.71(2H, t, J=4.5Hz), 9.13(1H, d, J=2.3Hz), 9.34(1H, d, J=2.3Hz)

IR (KBr)νcm$^{-1}$: 3084, 2900, 1346.

Elemental Analysis (for C$_8$H$_9$N$_3$O$_6$):
Calculated: C: 39.51%, H: 3.73%, N: 17.28%
Found: C: 39.44%, H: 3.64%, N: 17.42%

(2) Preparation of 3,5-diamino-2-(2-methoxyethoxy)pyridine dihydrochloride

The title compound was prepared in the same manner as in Synthesis Example 1 (2) (yield: 60%; purified over silica gel column chromatography using Silica gel 60 (manufactured by Merk Co.) and 20:1 ethyl acetate-methanol mixture as the eluent).

m.p. 158.5–159.6° C.

$^1$H-NMR (200 MHz, DMSO-d$_6$)δppm; 3.31(3H, s), 3.69(2H, t, J=4.5Hz), 4.40(2H, t, J=4.5Hz), 4.82(6H, s(br)), 7.04(1H, s(br)), 7.46(1H, s(br))

IR (KBr)νcm$^{-1}$: 3388, 3296, 3180, 2840, 2570.

Elemental Analysis (for C$_8$H$_{15}$N$_3$O$_2$Cl$_2$).
Calculated: C: 37.52%, H: 5.90%, N: 16.41%, Cl: 27.68%.
Found: C: 37.35%, H: 5.73%, N: 16.34%, Cl: 27.87%.

Synthetic Example 3

(1) Preparation of 2-(2-ethoxyethoxy)-3,5-dinitropyridine

The title compound was prepared in the same manner as in Synthesis Example 2 (1) (yield: 89%; purified over silica gel column chromatography using Silica gel 60 (manufactured by Merk Co.) and 1:1 chloroform-hexane mixture as the eluent).

Yellow oily substance
$^1$H-NMR (200 MHz, CDCl$_3$)δppm; (1.22(3H, t, J=7.0Hz), 3.61(2H, q, J=7.0Hz), 3.85-3.90(2H, m), 4.77-4.81(2H, m), 9.05(1H, d, J=2.6Hz), 9.26(1H, d, J=2.6Hz).
IR (film)νcm$^{-1}$: 3096, 2980, 1608, 1524, 1338.
Elemental Analysis (for C$_9$H$_{11}$N$_3$O$_6$):
Calculated: C: 42.03%, H: 4.31%, N: 16.34%.
Found: C: 41.77%, H: 4.24%, N: 16.40%.

(2) Preparation of 3,5-diamino-2-(2-ethoxyethoxy)pyridine dihydrochloride

The title compound was prepared in the same manner as in Synthesis Example 1 (2) (yield: 61%; purified over silica gel column chromatography using Silica gel 60 (manufactured by Merk Co.) and ethyl acetate as the eluent).

m.p. 143.2-144.8° C. (decomposed). $^1$H-NMR (200 MHz, DMSO-d$_6$)δppm; 1.11(3H, t, J=7.0Hz), 3.49(2H, q, J=7.0Hz), 3.71(2H, t, J=4.8Hz), 4.38(2H, t, J=4.8Hz), 3.9-5.2(6H, s(br)), 6.95(1H, s), 7.39(1H, s).
IR (KBr)νcm$^{-1}$: 3392, 3164, 2784, 2568, 1576.
Elemental Analysis (for C$_9$H$_{17}$N$_3$O$_2$Cl$_2$).
Calculated: C: 40.01%, H: 6.34%, N: 15.55%, Cl: 26.25%.
Found: C: 39.99%, H: 6.28%, N: 15.20%, Cl: 25.73%.

Synthetic Example 4

(1) Preparation of 3-oxa-5-(3,5-dinitro-2-pyridyloxy)-pentanol

The title compound was prepared in the same manner as in Synthesis Example 2 (1) (yield: 75%; purified over silica gel column chromatography using Silica gel 60 (manufactured by Merk Co.) and 2:1 ethyl acetate-hexane mixture as the eluent).

Yellow oily substance.
$^1$H-NMR (200 MHz, CDCl$_3$)δppm; 2.21(3H, t, J=6.0Hz), 3.67-3.75(4H, m), 3.94-3.98(2H, m), 4.79-4.84(2H, m), 9.07(1H, d, J=2.5Hz), 9.26(1H, d, J=2.5Hz)
IR (film)νcm$^{-1}$: 3588, 2928, 1610, 1538, 1338.
Elemental Analysis (for C$_9$H$_{11}$N$_3$O$_7$).
Calculated: C: 39.57%, H: 4.06%, N: 15.38%.
Found: C: 39.09%, H: 4.03%, N: 15.34%.

(2) Preparation of 3-oxa-5-(3,5-diamino-2-pyridyloxy)-pentanol dihydrochloride The title compound was prepared in the same manner in Synthesis Example 1 (2) (yield: 55%; purified over silica gel column chromatography using Silica gel 60 (manufactured by Merk Co.) and ethyl acetate-ethyl acetate:methanol (10:1) as the eluent).

m.p. 157.3-157.4° C. (decomposed).
$^1$H-NMR (200 MHz, DMSO-d$_6$)δppm; 3.94(4H, s(br)), 3.75(2H, t, J=4.6Hz), 4.38(2H, q, J=4.6Hz), 6.97(1H, d, J=2.0Hz), 7.41(1H, d, J=2.0Hz)
IR (KBr)νcm$^{-1}$: 3388, 3284, 3172, 2832, 1574.
Elemental Analysis (for C$_9$H$_{17}$N$_3$O$_3$Cl$_2$).
Calculated: C: 37.78%, H: 5.99%, N: 14.68%, Cl: 24.78%.
Found: C: 37.49%, H: 5.92%, N: 14.37%, Cl: 24.53%.

Synthetic Example 5

(1) Preparation of 2-(3,6-dioxaheptyloxy)-3,5-dinitropyridine

The title compound was prepared in the same manner as in Synthesis Example 2 (1) (yield: 70%; purified over silica gel column chromatography using Silica gel 60 (manufactured by Merk Co.) and 1:1 chloroform-hexane mixture as the eluent).

Yellow oily substance.
$^1$H-NMR (200 MHz, CDCl$_3$)δppm; 3.38(3H, s), 3.54-3.58(2H, m), 3.72-3.76(2H, m), 3.98-3.98(2H, m), 4.78-4.83(2H, m), 9.06(1H, d, J=2.6Hz), 9.25(1H, d, J=2.6Hz).
IR (film)νcm$^{-1}$: 3092, 2888, 1612, 1542, 1340.
Elemental Analysis (for C$_{10}$H$_{15}$N$_3$O$_7$).
Calculated: C: 41.82%, H: 4.56%, N: 14.63%.
Found: C: 41.51%, H: 4.45%, N: 14.63%.

(2) Preparation of 3,5-diamino-2-(3,6-dioxaheptyloxy)-pyridine dihydrochloride The title compound was prepared in the same manner as in Synthesis Example 1 (2) (yield: 48%; purified over silica gel column chromatography using Silica gel 60 (manufactured by Merk Co.) and ethyl acetate:methanol (20:1) as the eluent).

m.p. 138.2-139.6° C. (decomposed).
$^1$H-NMR (200 MHz, DMSO-d$_6$)δppm; 3.24(3H, s), 3.44(2H, t, J=4.7Hz), 3.58(2H, t, J=4.7Hz), 3.75(2H, t, J=4.5Hz), 4.38(2H, t, J=4.5Hz), 6.96(1H, d, J=2.2Hz), 4.5-6.0(6H, s(br)), 7.40(1H, d, J=2.2Hz),
IR (KBr)νcm$^{-1}$: 3388, 3164, 2732, 2584, 1572.
Elemental Analysis (for C$_{10}$H$_{19}$N$_3$O$_3$Cl$_2$).
Calculated: C: 40.01%, H: 6.38%, N: 14.00%, Cl: 23.62%.
Found: C: 39.26%, H: 6.23%, N: 13.70%, Cl: 21.65%.

Synthetic Example 6

(1) Preparation of 2-(2-butoxyethyoxy)-3,5-dinitropyridine

The title compound was prepared in the same manner as in Synthesis Example 2 (1) (yield: 76%; purified over silica gel column chromatography using Silica gel 60 (manufactured by Merk Co.) and 8:1 ethyl acetate-hexane mixture as the eluent).

Yellow oily substance.
1H-NMR (200 MHz, CDCl$_3$)δppm; 0.91(3H, t, J=7.3Hz), 1.27-1.45(2H, m), 1.50-1.64(2H, m), 3.55(2H, t, J=6.5Hz), 3.86(2H, t, J=4.7Hz), 4.79(2H, t, J=4.7Hz), 9.05(1H, d, J=2.5Hz), 9.26(1H, d, J=2.5Hz)
IR (film)νcm$^{-1}$: 1611, 1545, 1341.
Elemental Analysis (for C$_{11}$H$_{15}$N$_3$O$_6$).
Calculated: C: 46.32%, H: 5.30%, N: 14.73%.
Found: C: 46.21%, H: 5.23%, N: 14.71%.

(2) Preparation of 3,5-diamino-2-(2-butoxyethoxy)pyridine hydrochloride

The title compound was prepared in the same manner as in Synthesis Example 1 (2) (yield: 45%; purified over silica gel column chromatography using Silica gel 60

(manufactured by Merk Co.) and 2:1 ethyl acetate:hexane mixture as the eluent).

m.p. 139.5-143° C. (decomposed).

$^1$H-NMR (200 MHz, DMSO-d$_6$)δppm; 0.87(3H, t, J=7.2Hz), 1.21-1.55(4H, m), 3.44(2H, t, J=6.4Hz), 3.71(2H, t, J=4.8Hz), 4.40(2H, t, J=4.8Hz), 7.08(1H, d, J=2.4Hz), 7.49(1H, d, J=2.4Hz)

IR (KBr)νcm$^{-1}$: 3308, 2912, 1566.

Elemental Analysis (for C$_{11}$H$_{21}$N$_3$O$_2$Cl$_2$).

Calculated C: 44.30%, H: 7.10%, N: 14.09%, Cl: 23.78%.

Found: C: 44.22%, H: 7.15%, N: 14.09%, Cl: 23.34%.

Synthetic Example 7

(1) Preparation of 3,6,9-trioxa-11-(3,5-dinitro-2-pyridyloxy)undecanol

The title compound was prepared in the same manner as in Synthesis Example 2 (1) (yield: 66%; purified over silica gel column chromatography using Silica gel 60 (manufactured by Merk Co.) and 2:1 ethyl acetate-hexane mixture as the eluent).

Yellow oily substance.

$^1$H-NMR (200 MHz, CDCl$_3$)δppm; 2.48-2.64(1H, t(br)), 3.57-3.78(12H, m), 3.93-3.97(2H, m), 4.78-4.83(2H, m), 9.06(1H, d, J=2.6Hz), 9.26(1H, d, J=2.6Hz)

IR (film)νcm$^{-1}$: 3468, 2880, 1738, 1610, 1548, 1342.

Elemental Analysis (for C$_{13}$H$_{19}$N$_3$O$_9$).

Calculated: C: 43.22%, H: 5.30%, N: 11.63%.

Found: C: 42.73%, H: 5.26%, N: 11.52%.

(2) Preparation of 3,6,9-trioxa-11-(3,5-diamino-2-pyridyloxy)undecanol dihydrochloride The title compound was prepared in the same manner as in Synthesis Example 1 (2) (yield: 41%; purified over silica gel column chromatography using Silica gel 60 (manufactured by Merk Co.) and 10:1 ethyl acetate:methanol mixture as the eluent).

m.p. 135.3-135.7° C. (decomposed).

$^1$H-NMR (200 MHz, DMSO-d$_6$)δppm; 3.38-3.61(12H, m), 3.77(2H, t, J=4.9Hz), 4.40(2H, t, J=4.8Hz), 7.01(1H, d, J=2.4Hz), 7.43(1H, d, J=2.4Hz)

IR (KBr)νcm$^{-1}$: 3448, 3364, 3168, 2820, 1576.

Elemental Analysis (for C$_{13}$H$_{25}$N$_3$O$_5$Cl$_2$).

Calculated: C: 41.72%, H: 6.73%, N: 11.22%, Cl: 18.95%.

Found: C: 41.40%, H: 6.62%, N: 11.12%, Cl: 18.84%.

Synthetic Example 8

(1) Preparation of 2,2-bishydoxymethyl-3-(3,5-dinitro-2-pyridyloxy)propanol 0.6 g of sodium hydride (60% in oil, 14.7 mmol) was dispersed in 200 ml of dimethylformamide (dried in advance by Molecular Sieve 4A) under a nitrogen atmosphere, and to this dispersion was added 2 g of pentaerythritol by portions while stirring with a mechanical stirrer. After completion of the addition, the stirring was continued for 30 minutes, followed by an addition of 2 g of 2-chloro-3,5-dinitropyridine (9.8 mmol) by portions. The mixture was reacted for 30 minutes at room temperature and 2 hours at 80° C.

After cooling to the room temperature, dimethylformamide was evaporated under reduced pressure using a vacuum pump at 80° C. 6 ml of a saturated aqueous solution of ammonium chloride was added, followed by extraction with ethyl acetate. The extract was dried over anhydrous sodium sulfate. The solvent was removed by evaporation under reduced pressure and the residue was purified over silica gel column chromatography (Silica gel 60 manufactured by Merk Co. eluent: ethyl acetate:hexane=1:1-ethyl acetate) to obtain 1.2 g (4.0 mmol) an orange oil of the title compound (yield: 39%).

$^1$H-NMR (200 MHz, DMSO-d$_6$)δppm; 3.48(6H, d, J=5.2Hz), 4.48(3H, s and 2H, t, J=5.2Hz), 9.12(1H, d, J=2.5Hz), 9.26(1H, d, J=2.5Hz)

IR (film)νcm$^{-1}$: 3400, 1614, 1540, 1344.

Elemental Analysis (for C$_{10}$H$_{13}$N$_3$O$_8$).

Calculated: C: 39.61%, H: 4.32%, N: 13.86%.

Found: C: 39.42%, H: 4.46%, N: 13.35%.

(2) Preparation of 2,2-bishydoxymethyl-3-(3,5-diamino-2-pyridyloxy)-propanol dihydrochloride The title compound was prepared in the same manner as in Synthesis Example 1 (2) (yield: 49%; purified over silica gel column chromatography using Silica gel 60 (manufactured by Merk Co.) and 4:1 ethyl acetate:methanol mixture as the eluent).

m.p. 175.1-178.0° C. (decomposed).

$^1$H-NMR (200 MHz, DMSO-d$_6$)δppm; 3.48(6H, s), 4.13(2H, s), 4.4-5.5(6H, s(br)), 6.93(1H, d, J=2.3Hz), 7.38(1H, d, J=2.3Hz)

IR (KBr)νcm$^{-1}$: 3408, 3288, 3172, 1596, 1580, 1290, 1008, 990.

Elemental Analysis (for C$_{10}$H$_{19}$N$_3$O$_4$Cl$_2$).

Calculated: C: 37.99%, H: 6.06%, N:13.29%, Cl: 22.42%.

Found: C: 38.00%, H: 6.10%, N: 12.94%, Cl: 19.65%.

Example 1

| Composition of base components: | % |
|---|---|
| Oleic acid | 10 |
| Oleic acid diethanolamide | 8 |
| Oleyl alcohol | 2 |
| Polyoxyethylene octyldodecyl ether (Average EO: 20 mol) | 10 |
| Ethanol | 15 |
| Propylene glycol | 10 |
| Ammonium chloride | 3 |
| 25% Ammonia | 7 |
| Water | 35 |
| Total | 100 |

0.01 mol of the developing substance and 0.01 mol of the coupling substance listed in Table 1 were added to 100 g. of the above base component composition. The mixtures were adjusted to pH 9.5 by an addition of ammonia to produce dye compositions of the present invention.

Dye fluids were prepared from dye compositions of the present invention and equivalent amounts of 6% hydrogen peroxide aqueous solution. The fluids were applied to gray human hair and were allowed to stand for 30 minutes at 30° C. The hair was washed with a normal shampoo and dried. The color tone, the resistance to discoloration into brown, the resistance to shampooing of the dyed hairs were tested: The results are shown in Table 1, which demonstrate that all compositions exhibited excellent color tone and vividness in the color.

(1) Resistance color phading

The hair was stored under the conditions of 40° C., 75% RH and died at room temperature. The hair thus treated was compared by the naked eye with a tress of the dyed hair which had been stored at −5° C. The evaluation was made according to the following standard.

A: Little color change
B: Slight color change
C: Significant color change (2) Resistance to shampooing The hair was washed with a neutral shampoo for 15 times and compared with a tress of the dyed hair which was not washed.

A: Little discolor occurred
B: Slight discolor occurred
C: Significant discolor occurred Developing substance $P_1$: p-phenylenediamine
$P_2$: toluene-2,5diamine Coupling substance $C_1$: 3,5-diamino-2-methoxypyridine
$C_2$: 3,5-methoxypryridine dihydrochloride
$C_3$: 2-(3,5-diamino-2-pyridyloxy)ehtanol
$C_4$: 2-(3,5-diamino-2pyridyloxy)ethanol dihydrochloride
$C_5$: 2,6-diaminopyridine
$C_6$: 3,5-diamino-2-(2-methoxyethyoxy)pyridine dihydrochloride
$C_7$: 3,5-diamino-2-(2-ethoxyethyoxy)pyridine dihydrochloride
$C_8$: 3-oxa-5-(3,5-diamino-2-pyridyloxy)pentanol dihydrochloride
$C_9$: 3,5-diamino-2-(2-pyridyloxy) pyridine dihydrochloride
$C_{10}$: 3,5-diamino-2-(2-butoxyethyoxy)pyridine dihydrochloride
$C_{11}$: 3-(3,5-diamino-2-pyridyloxy)-2)hydroxypropanol dihydrochloride
$C_{12}$: 3,6,9-trioxa-11-(3,5-diamino-2-pyridyloxy)-undecanol dihydrochloride
$C_{13}$: 2,2-bishydoxymethyl-3-(3,5-diamino-2-pyridyloxy)-propanol dihydrochloride
$C_{14}$: m-Phenylenediamine

TABLE 1

| | Developing Substance | Coupling Substance | Color | Resistance to color phading | Resistance to Shampooing |
|---|---|---|---|---|---|
| Invention Composition | | | | | |
| No. 1 | $P_1$ | $C_1$ | Blue | A | A |
| No. 2 | $P_1$ | $C_2$ | Blue | A | A |
| No. 3 | $P_1$ | $C_3$ | Blue | A | A |
| No. 4 | $P_1$ | $C_4$ | Blue | A | A |
| No. 5 | $P_1$ | $C_6$ | Blue | A | A |
| No. 6 | $P_1$ | $C_7$ | Blue | A | A |
| No. 7 | $P_1$ | $C_8$ | Blue | A | A |
| No. 8 | $P_1$ | $C_9$ | Blue | A | A |
| No. 9 | $P_1$ | $C_{10}$ | Blue | A | A |
| No. 10 | $P_1$ | $C_{11}$ | Blue | A | A |
| No. 11 | $P_1$ | $C_{12}$ | Blue | A | A |
| No. 12 | $P_1$ | $C_{13}$ | Blue | A | A |
| No. 13 | $P_2$ | $C_1$ | Blue | A | A |
| No. 14 | $P_2$ | $C_2$ | Blue | A | A |
| No. 15 | $P_2$ | $C_3$ | Blue | A | A |
| No. 16 | $P_2$ | $C_4$ | Blue | A | A |
| No. 17 | $P_2$ | $C_6$ | Blue | A | A |
| No. 18 | $P_2$ | $C_7$ | Blue | A | A |
| No. 19 | $P_2$ | $C_8$ | Blue | A | A |
| No. 20 | $P_2$ | $C_9$ | Blue | A | A |
| No. 21 | $P_2$ | $C_{10}$ | Blue | A | A |
| No. 22 | $P_2$ | $C_{11}$ | Blue | A | A |
| No. 23 | $P_2$ | $C_{12}$ | Blue | A | A |
| No. 24 | $P_2$ | $C_{13}$ | Blue | A | A |
| Comparative Composition | | | | | |
| No. 1 | $P_1$ | $C_5$ | Blue | B | C |
| No. 2 | $P_1$ | $C_{14}$ | Blue | C | C |
| No. 3 | $P_2$ | $C_5$ | Blue | B | C |
| No. 4 | $P_2$ | $C_{14}$ | Blue | C | C |

Obviously, numerous modifications and variations of the present invention are possible in light of the above teachings. It is therefore to be understood that within the scope of the appended claims, the invention may be practiced otherwise than as specifically described herein.

What is claimed is:

1. A dye composition for keratinous fibers comprising a developing substance and, as a coupling substance, a 3,5-diaminopyridine derivative of the following formula (I),

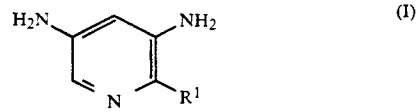

wherein $R^1$ is an alkoxy group or a group

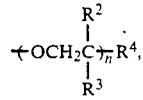

wherein $R^2$ and $R^3$ may be the same or different and individually represents a hydrogen atom or a hydroxyalkyl group, $r^4$ a hydroxy, alkoxy, or hydroxyalkyl group, and n is a number of 1–4; or a salt thereof.

2. A 3,5-diaminopyridine derivative of the following formula (II),

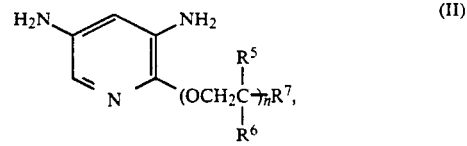

wherein $R^5$ and $R^6$ may be the same or different and individually represents a hydrogen atom or a hydroxyalkyl group, $R^7$ is a hydroxy, alkoxy, or hydroxyalkyl group, and n is a number of 1–4; or a salt thereof.

3. A 3,5-dinitropyridine derivative of the following formula (III),

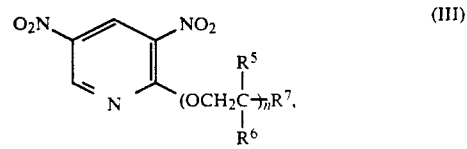

wherein $R^5$, $R^6$, $R^7$, and n have the same meanings as defined in formula (II); or a salt thereof.

* * * * *